United States Patent [19]

Miura et al.

[11] Patent Number: 4,532,210

[45] Date of Patent: Jul. 30, 1985

[54] PROCESS FOR PRODUCING HYDROGEN BY ALGA IN ALTERNATING LIGHT/DARK CYCLE AND ENVIRONMENTAL AEROBIC/MICROAEROBIC CONDITIONS

[76] Inventors: Yoshiharu Miura, 1-700, Megamiyama-cho, Koyoen, Nishinomiya, Hyogo, Osaka; Kazuhisa Miyamoto, 33-13, Higashi-Awaji 4-chome, Higashi-Yodogawa-ku, Osaka, Osaka; Kiyohito Yagi, Sakurai-so, 1-8-11, Niina, Minoo, Osaka, all of Japan

[21] Appl. No.: 424,767

[22] Filed: Sep. 27, 1982

[30] Foreign Application Priority Data

Oct. 8, 1981 [JP] Japan ................................. 56-161500
Feb. 4, 1982 [JP] Japan ................................. 57-17132

[51] Int. Cl.³ ............................................. C12P 3/00
[52] U.S. Cl. ........................................ 435/168; 47/1.4; 435/42; 435/232; 435/253; 435/946; 435/241
[58] Field of Search .................. 435/42, 168, 253, 257, 435/819, 848, 849, 946, 232; 47/1.4

[56] References Cited

U.S. PATENT DOCUMENTS 3,959,923 6/1973 Selke ........................................ 47/1.4
4,148,690 4/1979 Weetall ..................................... 435/946

OTHER PUBLICATIONS

Biochemistry of Industrial Micro-Organisms, Ed. by C. Rainbow and A. H. Rose, Academic Press, 1963, pp. 396-401, Elias Greenbaum, Science, vol. 125, 1/15/82, pp. 291-293.
Greenbaum, "Biotechnology and Bioengineering Symp.", No. 10, pp. 1-13 (1980).

Primary Examiner—Sam Rosen
Assistant Examiner—William J. Herald
Attorney, Agent, or Firm—Birch, Stewart, Kolasch & Birch

[57] ABSTRACT

Hydrogen is biologically, effectively produced by an alga in an alternating light/dark cycle which comprises alternating a step for cultivating the alga in water under aerobic conditions in the presence of light to accumulate photosynthetic products in the alga and a step for cultivating the alga in water under microaerobic conditions in the dark to decompose accumulated material by photosynthesis to evolve hydrogen.

31 Claims, 2 Drawing Figures

PROCESS FOR PRODUCING HYDROGEN BY ALGA IN ALTERNATING LIGHT/DARK CYCLE AND ENVIRONMENTAL AEROBIC/MICROAEROBIC CONDITIONS

BACKGROUND OF THE INVENTION

The present invention relates to a process for producing hydrogen by algae in an alternating light/dark cycle.

Hydrogen is one of the noteworthy clean energy sources which will be able to take the place of fossil fuel such as petroleum and coal. Hydrogen has various advantages as an energy source such that (1) it can be converted to electric energy effectively by means of a fuel cell, (2) its calorie per unit weight is 3 to 4 times of that of petroleum, and it burns to form only water so that it does not pollute the environment, and (3) water, which is one of the raw materials for producing hydrogen, is inexhaustible.

The processes for the production of hydrogen by means of solar energy are classified into two classes, one of which is a non-biological process using semiconductors and the other of which is a biological process using photosynthetic products. With respect to the latter biological process, there proposed some systems for biophotolyzing water to produce hydrogen by controlling the metabolism of higher plants and algae having the ability to decompose water or by combining said higher plants and algae with a microorganism having the ability to decompose water. However, in conventional systems, oxygen produced by photolysis of water deactivates or prohibits the activity of the hydrogen producing system (i.e. hydrogenase), which results in unstability in the production of hydrogen. Further, isolation and purification of hydrogen is difficult, and there is a possibility of explosion of a gaseous mixture of oxygen and hydrogen. Therefore, the conventional systems are not practical.

SUMMARY OF THE INVENTION

As a result of an extensive study to biologically produce hydrogen with good productivity and durability, it has now been found that in a certain system, hydrogen is effectively produced by temporary separation of oxygen and hydrogen.

According to the present invention, there is provided a process for producing hydrogen by an alga in an alternating light/dark cycle which comprises alternating a step for cultivating the alga in water under light aerobic conditions to accumulate photosynthetic products in the alga and a step for cultivating the alga in water under dark microaerobic conditions to decompose accumulated material by photosynthesis to evolve hydrogen.

The alga may be any alga which has ability to produce hydrogen. Preferably, a green alga having such ability (e.g. *Chlamydomonas reinhardtii*) and a blue-green alga having such ability (e.g. *Synechococcus sp.*) are used. The alga in any growth phase may be used. Preferably, the alga in a logarithmic growth phase, particularly in a midlogarithmic growth phase is used, since the alga in these growth phases produces hydrogen more effectively under the dark microaerobic conditions.

In the process of the invention, during the cultivation of the alga in the light aerobic conditions, organic materials (e.g. starch) are accumulated in the alga, and during the cultivation of the alga in the dark microaerobic conditions, the accumulated organic materials are decomposed to evolve hydrogen.

The cultivation in the light aerobic conditions is carried out in a medium containing adequate inorganic components in light with the passing of air through the medium. The cultivation temperature is usually from 15° to 70° C. Preferably, in case of the green alga, it is from 15° to 40° C., particularly from 25° to 35° C., and in case of the blue-green alga, from 15° to 60° C., particularly from 40° to 55° C. Addition of 2 to 5% by volume of carbon dioxide in air to be passed through preferably increases the amount of the accumulated organic materials. Preferred examples of the medium are modified Bristol medium (hereinafter referred to as "MBM") for the green alga, and modified Detmer medium (hereinafter referred to as "MDM") and BG-11 medium for the blue-green alga.

The compositions of these mediums are as follows:

| Composition of MBM | |
|---|---|
| $MgSO_4.7H_2O$ | 75 mg/l |
| $CaCl_2.2H_2O$ | 10 mg/l |
| $K_2HPO_4$ | 75 mg/l |
| $KH_2PO_4$ | 175 mg/l |
| NaCl | 25 mg/l |
| $FeSO_4.7H_2O$ | 2.0 mg/l |
| Trace-metal mixture $A_5$*[1] | 1.0 ml/l |
| $Na_2CO_3$ | 53 mg/l |
| $NH_4Cl$ | 268 mg/l |
| Composition of MDM (pH 8.0) | |
| $KNO_3$ | 1.0 g/l |
| $CaCl_2.2H_2O$ | 0.1 g/l |
| $MgSO_4.7H_2O$ | 0.25 g/l |
| NaCl | 0.1 g/l |
| $K_2HPO_4$ | 0.25 g/l |
| $FeSO_4.7H_2O$ | 0.02 g/l |
| Trace-metal mixture $A_5$*[1] | 1.0 ml/l |
| Composition of BG-11 medium (pH 7.0) | |
| $NaNO_3$ | 1.5 g/l |
| $K_2HPO_4$ | 0.04 g/l |
| $MgSO_4.7H_2O$ | 0.075 g/l |
| $CaCl_2.2H_2O$ | 0.036 g/l |
| Citric acid | 0.006 g/l |
| Ferric ammonium citrate | 0.006 g/l |
| EDTA(disodium magnesium salt) | 0.006 g/l |
| $Na_2CO_3$ | 0.02 g/l |
| Trace-metal mixture $A_5$*[1] | 1.0 g/l |

*[1] The trace mixture $A_5$ contains 2.86 g of $H_3BO_4$, 1.81 g of $MnCl_2.4H_2O$, 0.22 g of $ZnSO_4.7H_2O$, 0.08 g of $CuSO_4.5H_2O$, 0.021 g of $Na_2MoO_4$, 1 drop of conc. $H_2SO_4$ in 1 l of deionized water.

The cultivation under the dark microaerobic conditions is carried out in a light-shielded vessel containing the same medium as described above in an atmosphere of nitrogen containing a micro amount of oxygen. The amount of oxygen in nitrogen varies with other cultivation conditions. Since too much oxygen may inhibit the hydrogen producing system, usually not more than 0.10% by volume of oxygen is added in nitrogen. However, at the beginning of the cultivation under the dark microaerobic conditions, addition of not more than 0.30% by volume, preferably not more than 0.23% by volume of oxygen in nitrogen preferably increases the rate of hydrogen evolution.

The hydrogen evolution amount can be increased by agitating or shaking the medium.

The light/dark cycle may be an artificial cycle and preferably corresponds to a day/night cycle.

The process of the invention not only produces hydrogen very economically and effectively by utilizing the solar energy, but also produces useful organic materials, i.e. biomasses, by recovering the alga grown under the light conditions. Under the dark conditions, in addition to the production of hydrogen by the decomposition of the starch; ethanol, glycerol, formic acid, acetic acid, lactic acid, etc. are accumulated in the medium and recovered. Further, when these organic materials are decomposed to produce hydrogen by *E. coli* or photosynthetic bacteria which uses these materials as substrates, the productivity of hydrogen is greatly improved.

For example, *E. coli* decomposes formic acid with an enzyme system so called formic hydrogenlyase to produce hydrogen. The enzyme system is induced in the presence of glucose and casamino acid under anaerobic conditions. The induced amount of the enzyme system, however, greatly varies with the anaerobic degree and no enzyme is induced in aerobic conditions. As a result of an extensive study to induce the enzyme system in *E. coli* under aerobic conditions, it has been found that the addition of formate (e.g. sodium formate) as an inducer and sodium succinate as an electron donor for aerobic respiration induces *E. coli* to produce formic hydrogenlyase in amounts as high as induced anaerobically.

DETAILED DESCRIPTION OF THE INVENTION

The present invention will be hereinafter explained further in detail by the following examples.

EXAMPLE 1

Cultivation under light conditions

A green alga (*Chlamydomonas reinhardtii*) was added in a 1 l bottle containing 700 ml of MBM in the concentration of 3.5 $\mu$g.dry wt./ml and grown under air at a light intensity of 18 W/cm$^2$ at about 30° C. while air containing 5% by volume of carbon dioxide was passed through the medium at a rate of 0.5 l/min.

Dark hydrogen evolution

After growth of the alga, nitrogen was flushed in the bottle to make the interior microaerobic. Then, the bottle was shielded from light and the alga was cultivated at about 30° C. under stirring. The amount of evolved hydrogen was measured by gas chromatography.

The above described cultivation under light conditions and the dark hydrogen evolution were alternatively cycled for 12 hours.

Figure 1:
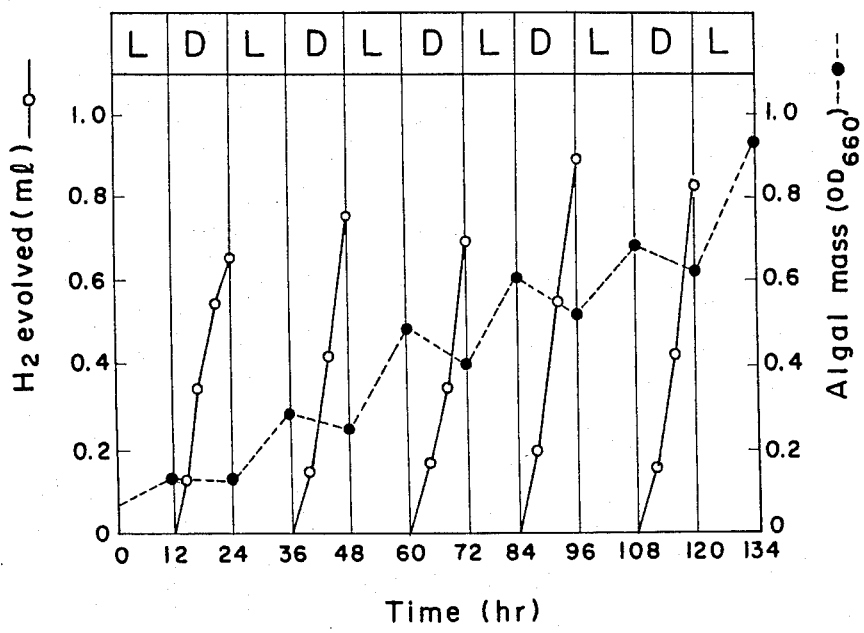
FIG. 1 is a chart which plots the hydrogen evolution versus time for the experiment reported in Example 1.

The results are shown in FIG. 1 in which o denotes the amount (ml) of evolved hydrogen in the dark period and • denotes the algal mass represented by OD$_{660}$.

From the results, it is understood that a nearly constant amount of hydrogen was evolved in every dark period but the amount does not increase with the increase of the algal mass. This may result from the aging of the alga and limited supply of light energy per unit area which results in the decrease of the amount of starch accumulated per unit weight of the alga.

EXAMPLE 2

Figure 2:
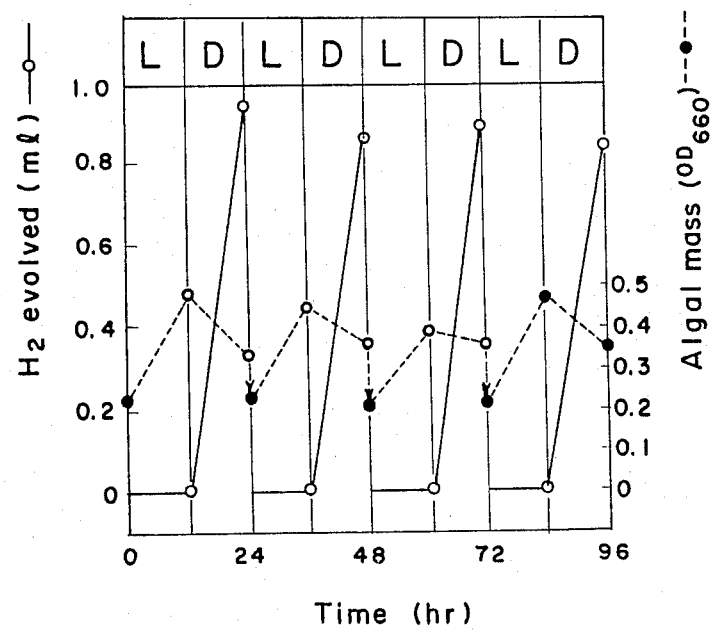
FIG. 2 is a chart which plots the hydrogen evolution versus time for the experiment reported in Example 2.

In the same manner as in Example 1, but removing a part of the alga from the bottle after the dark hydrogen evolution and before the cultivation under the light conditions, the cyclic cultivation of the alga was carried out. The result are shown in FIG. 2.

EXAMPLE 3 AND COMPARATIVE EXAMPLES 1 AND 2

*E. coli* IFO 12713 (corresponding to 10 g of dry weight) was added to a substrate medium containing an inducer and shook at 35° C. for 2 hours under nitrogen or air atmosphere.

The substrate used in Example 3 comprised sodium formate (50M), sodium succinate (10 mM), casamino acid (0.2%) and potassium phosphate buffer (pH 7.0, 20 mM) and in Comparative Examples, glucose (50 mM), casamino acid (0.2%) and potassium phosphate buffer (pH 7.0, 20 mM). After 2 hours induction, the cells were collected and washed with phosphate buffer twice. The cells were added in a solution of 50 mM sodium formate, the gas phase was replaced with nitrogen and the mixture was shaken at 35° C. Formic hydrogenlyase activity was determined by measuring the amount of evolved hydrogen. The results are shown in Table 1.

TABLE 1

| | Inducer | Condition | Amount of formic hydrogenlyase (unit*[1]/mg. dry wt.) |
|---|---|---|---|
| Example 3 | Sodium formate + sodium succinate | Aerobic | 12 |
| Comparative Example 1 | Glucose | Anaerobic | 13 |
| Comparative Example 2 | Glucose | Aerobic | 0 |

Note *[1] 1 unit is an amount of the enzyme which produces 1 $\mu$mole of hydrogen per 1 hour by using formic acid as a substrate.

*Chlamydomonas reinhardtii* was cultivated under the dark conditions for 12 hours in the same manner as in Example 1 and thereafter the alga was removed by centrifugation. The supernatant was fed to *E. coli* in which formic hydrogenlyase had been aerobically induced as in Example 3. Hydrogen (0.63 $\mu$mole) was evolved from the supernatant containing formic acid (0.7 $\mu$mole).

EXAMPLE 4

Cultivation under light conditions

A single cell thermophilic blue-green alga (Synechococcus sp.) obtained from the Beppu hot spring (Ooita, Japan) was added in 1 l flask containing 500 ml of BG-11 medium and grown under a fluorescent lamp while the flask was reciprocally shaken at a rate of 100 rpm in a constant temperature room kept at 45° C.

Dark hydrogen evolution

When the algal concentration reached about 20 $\mu$g dry wt./ml, the alga was collected by centrifugation, washed with BG-11 medium twice and resuspended in the same medium (10 ml). The algal concentration was 0.17 mg/ml. The suspension was charged in a light-shielded 34 ml test tube and sealed with a rubber cap. The gas phase was replaced with nitrogen and a predetermined amount of oxygen was flushed by means of a syringe. The test tube was reciprocally shaken at a rate of 100 rpm in a constant temperature bath kept at 45° C.

After 2, 6.5, 12 and 20 hours of shaking, each 500 μl of a gas phase sample was collected and its composition was analyzed by gas chromatography.

The results are shown in Table 2.

TABLE 2

| Oxygen content in gas phase (% by vol.) | Amount of evolved hydrogen (μg/mg. dry wt.) Shaking time (hr.) | | | |
|---|---|---|---|---|
| | 2 | 6.5 | 12 | 20 |
| 0.08 | 0 | 0 | 0 | 0 |
| 0.3 | 0 | 2 | 14 | 28 |

What is claimed is:

1. A process for producing hydrogen by an alga in an alternating light/dark cycle, comprising the steps of:
   alternately cultivating the alga in water under aerobic conditions in the presence of light to accumulate photosynthesis products including starch in the alga and cultivating the alga in water under microaerobic conditions in the dark to decompose accumulated material including starch by photosynthesis to evolve hydrogen; and
   recovering the thus evolved hydrogen.

2. The process according to claim 1, wherein a gaseous mixture of air and carbon dioxide is passed through the water in the step for cultivating the alga under the aerobic conditions in the presence of light.

3. The process according to claim 2, wherein the carbon dioxide and air which is passed through the water is present in a volume ratio of from 0:100 to 10:90.

4. The process according to claim 1, wherein the cultivation under the microaerobic condition in the dark is initiated in the presence of not more than 0.30% by volume of oxygen in a gas phase and carried out in an atmosphere of nitrogen containing not more than 0.30% by volume of oxygen.

5. The process according to claim 1, wherein the alga is introduced when the alga is in a logarithmic growth phase.

6. The process according to claim 5, wherein the alga is introduced when the alga is in a midlogarithmic growth phase.

7. The process according to claim 1, wherein the alga is a green alga.

8. The process according to claim 7, wherein the green alga is *Chlamydomonas reinhardtii*.

9. The process according to claim 7, wherein the cultivation is carried out in each step at a temperature of from 15° to 40° C.

10. The process according to claim 9, wherein the cultivation temperature in each step is from 7° to 35° C.

11. The process according to claim 1, wherein the alga is a blue-green alga.

12. The process according to claim 11, wherein the blue-green alga is *Synechococcus* sp.

13. The process according to claim 11, wherein the cultivation is carried out in each step at a temperature of from 15° to 70° C.

14. The process according to claim 13, wherein the cultivation temperature in each step is from 40° to 50° C.

15. The process according to claim 1, wherein the cultivation under the microaerobic conditions in the dark is carried out with agitation or shaking.

16. The process according to claim 1, wherein the time periods of the light/dark cycle correspond to a day/night cycle.

17. The process according to claim 1, which further comprises incubating *E. coli* with formic acid which is produced by the alga under the microaerobic conditions in the dark and which has accumulated in the medium to thereby produce hydrogen.

18. The process according to claim 17, wherein formic hydrogenlyase produced by said *E. coli* is induced by aerobic incubation of *E. coli* in the presence of formate and sodium succinate.

19. A process for producing hydrogen by an alga in an alternating light/dark cycle, comprising the steps of:
   alternately cultivating a hydrogen producing alga in an aqueous nutrient medium containing an organic material capable of being decomposed by said alga into hydrogen under aerobic conditions in the presence of light for a time sufficient to accumulate products of photosynthesis and cultivating the alga in the dark under a nitrogen atmosphere containing added oxygen in an amount of not more than 0.30% by volume to decompose said organic material by photosynthesis to evolve hydrogen; and
   recovering the thus evolved hydrogen.

20. The process according to claim 19, wherein said organic material is starch.

21. The process according to claim 19, wherein said nitrogen containing atmosphere contains not more than 0.23% by volume of oxygen.

22. The process according to claim 19, wherein said nitrogen containing atmosphere contains not more than 0.10% by volume of oxygen.

23. The process according to claim 19, wherein said products of photosynthesis include at least one compound selected from the group consisting of ethanol, glycerol, formic acid, acetic acid and lactic acid.

24. The process according to claim 19, wherein formic acid is produced as a product of photosynthesis during cultivation in the dark and wherein the formic acid is incubated with *E. coli* capable of producing formic hydrogenlyase whereby additional hydrogen is produced.

25. The process according to claim 20, wherein the alga is introduced when the alga is in a midlogarithmic growth phase.

26. The process according to claim 19, wherein the alga is *Synechococcus* sp.

27. The process according to claim 19, wherein the alga is *Chlamydomonas reinhardtii*.

28. A process for producing hydrogen by a microorganism in an alternating light/dark cycle, comprising the steps of:
   alternately cultivating a hydrogen producing microorganism selected from the group consisting of *Chlamydomonas reinhardtii* and *Synechococcus* sp. in an aqueous nutrient medium containing starch at a temperature of 15° to 70° C. under aerobic conditions and in the presence of light with the addition of a gaseous mixture of air and carbon dioxide for a time sufficient to accumulate products of photosynthesis and cultivating the microorganism in the dark under a nitrogen atmosphere containing added oxygen in an amount of not more than 0.30% by volume to decompose said starch to evolve hydrogen; and
   recovering the thus evolved hydrogen.

29. The process according to claim 28, wherein said microorganism is *Chlamydomonas reinhardtii* and a portion of said *Chlamydomonas reinhardtii* is removed from the media after each light/dark cycle.

30. The process according to claim 28, which further comprises incubating *E. coli* with formic acid which is produced by said *Chlamydomonas reinhardtii* to produce hydrogen.

31. The process according to claim 28, wherein said microorganism is *Synechococcus* sp.

* * * * *